United States Patent [19]
Laufer

[11] Patent Number: 6,004,316
[45] Date of Patent: Dec. 21, 1999

[54] METHOD FOR THE TREATMENT OF PATENT DUCTUS ARTERIOSUS

[75] Inventor: Michael D. Laufer, Menlo Park, Calif.

[73] Assignee: Hearten Medical, Inc., Tustin, Calif.

[21] Appl. No.: 09/158,348

[22] Filed: Sep. 21, 1998

Related U.S. Application Data

[63] Continuation of application No. 08/739,820, Oct. 30, 1996, Pat. No. 5,827,268.

[51] Int. Cl.$^6$ .................................................. A61B 17/34
[52] U.S. Cl. .............................. 606/28; 606/41; 606/46; 606/47; 128/898
[58] Field of Search ........................ 604/213; 606/27–32, 606/41, 45, 46–48; 607/96, 98, 99, 116, 122; 600/373, 374, 381; 128/898

[56] References Cited

U.S. PATENT DOCUMENTS

| | | |
|---|---|---|
| 373,399 | 11/1887 | Hamilton . |
| 4,140,130 | 2/1979 | Storm, III ............................... 128/404 |
| 4,196,734 | 4/1980 | Harris . |
| 4,765,331 | 8/1988 | Petruzzi et al. ..................... 128/303.14 |
| 4,807,620 | 2/1989 | Strul et al. ............................ 128/303.1 |
| 4,865,047 | 9/1989 | Chou et al. ............................... 128/784 |
| 4,989,617 | 2/1991 | Memberg et al. ....................... 128/785 |
| 5,041,109 | 8/1991 | Abele . |
| 5,057,106 | 10/1991 | Kasevich et al. ........................ 128/804 |
| 5,103,804 | 4/1992 | Abele et al. . |
| 5,114,423 | 5/1992 | Kasprzyk et al. ........................... 606/27 |
| 5,133,365 | 7/1992 | Heil, Jr. et al. ........................... 128/786 |
| 5,143,063 | 9/1992 | Fellner ..................................... 128/399 |
| 5,176,135 | 1/1993 | Fain et al. ............................ 128/419 D |
| 5,190,517 | 3/1993 | Zieve et al. ................................. 604/22 |
| 5,259,394 | 11/1993 | Bens ........................................ 607/127 |
| 5,261,878 | 11/1993 | Galindo ..................................... 604/96 |
| 5,281,218 | 1/1994 | Imran ........................................ 606/41 |
| 5,295,955 | 3/1994 | Rosen et al. ............................... 604/22 |
| 5,303,719 | 4/1994 | Wilk et al. ................................ 128/898 |
| 5,314,466 | 5/1994 | Stern et al. ............................... 607/156 |
| 5,334,217 | 8/1994 | Das ........................................... 606/213 |
| 5,364,389 | 11/1994 | Anderson ................................... 606/15 |
| 5,370,677 | 12/1994 | Rudie et al. ............................. 607/101 |
| 5,370,678 | 12/1994 | Edwards et al. ......................... 607/101 |
| 5,383,926 | 1/1995 | Lock et al. .................................. 623/1 |
| 5,405,346 | 4/1995 | Grundy et al. ............................. 606/41 |
| 5,425,744 | 6/1995 | Fagan et al. ............................. 606/213 |
| 5,431,649 | 7/1995 | Mulier et al. .............................. 606/41 |
| 5,433,727 | 7/1995 | Sideris ..................................... 606/213 |
| 5,437,664 | 8/1995 | Cohen et al. ............................... 606/42 |
| 5,447,529 | 9/1995 | Marchlinski et al. ..................... 607/99 |
| 5,451,235 | 9/1995 | Lock et al. ............................... 606/213 |
| 5,454,807 | 10/1995 | Lennox et al. ............................. 606/15 |
| 5,454,809 | 10/1995 | Janssen .................................... 606/41 |
| 5,458,596 | 10/1995 | Lax et al. .................................. 606/31 |
| 5,462,545 | 10/1995 | Wang et al. ............................... 606/41 |
| 5,478,330 | 12/1995 | Imran et al. . |
| 5,486,193 | 1/1996 | Bourne et al. ........................... 606/194 |
| 5,507,811 | 4/1996 | Koike et al. ............................... 623/11 |
| 5,522,873 | 6/1996 | Jackman et al. ......................... 607/122 |
| 5,540,679 | 7/1996 | Fram et al. ................................. 606/27 |
| 5,545,193 | 8/1996 | Fleischman et al. . |
| 5,545,195 | 8/1996 | Lennox et al. ........................... 607/105 |
| 5,575,810 | 11/1996 | Swanson et al. .......................... 607/99 |

Primary Examiner—Linda C. M. Dvorak
Assistant Examiner—David Ruddy
Attorney, Agent, or Firm—Burns, Doane, Swecker & Mathis, LLP

[57] ABSTRACT

A device and method for treating patent ductus arteriosus in a human. A catheter having a collapsible/expandable heating element at a distal end for entering an infant transcutaneously and being advanced to the ductus arteriosus. A method of heating the inner surface of the ductus arteriosus with the heating element to a temperature sufficient to produce a material change in the collagen of the ductus arteriosus such that the ductus arteriosus passage shrinks to closure.

11 Claims, 9 Drawing Sheets

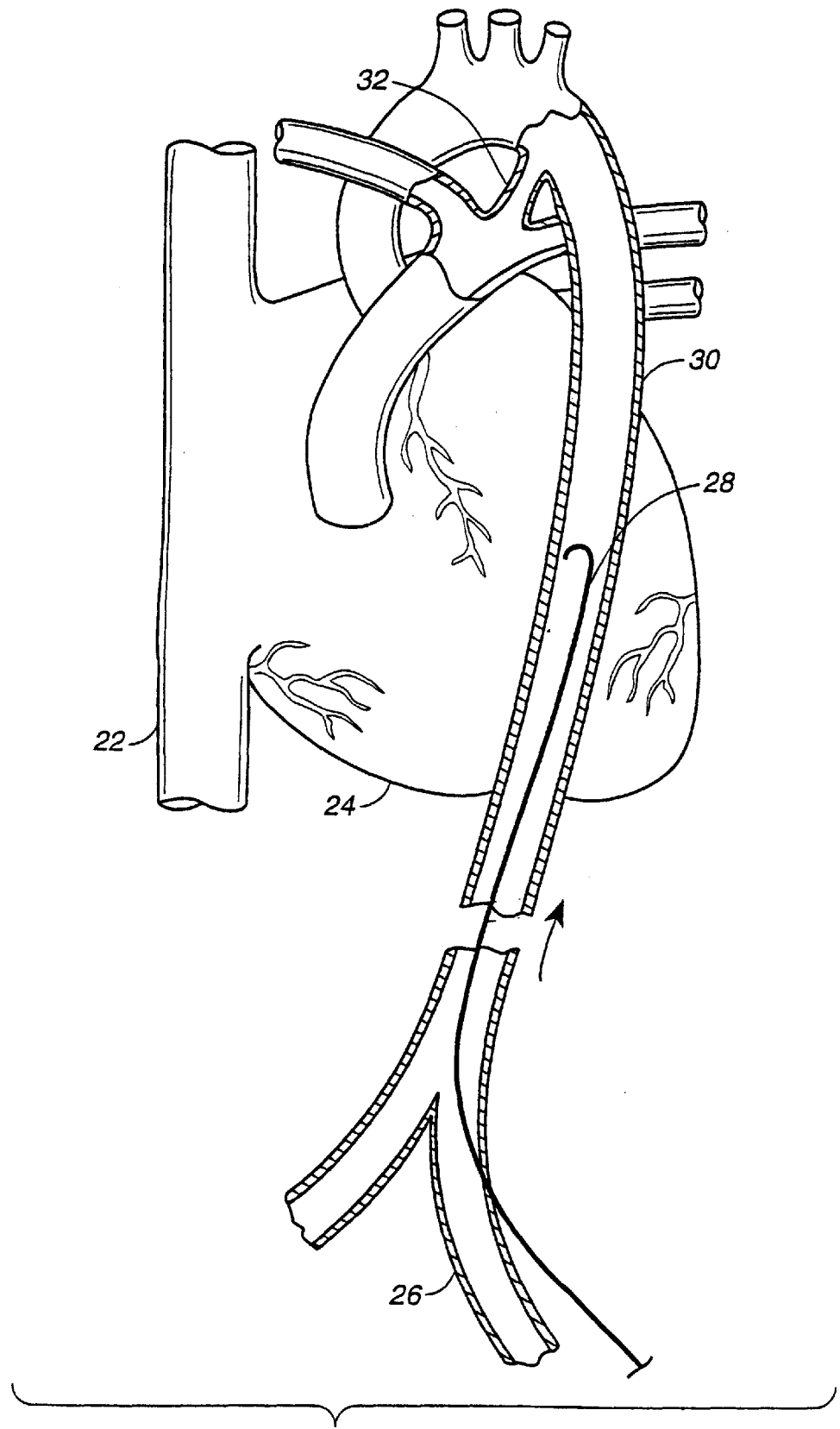
FIG._1

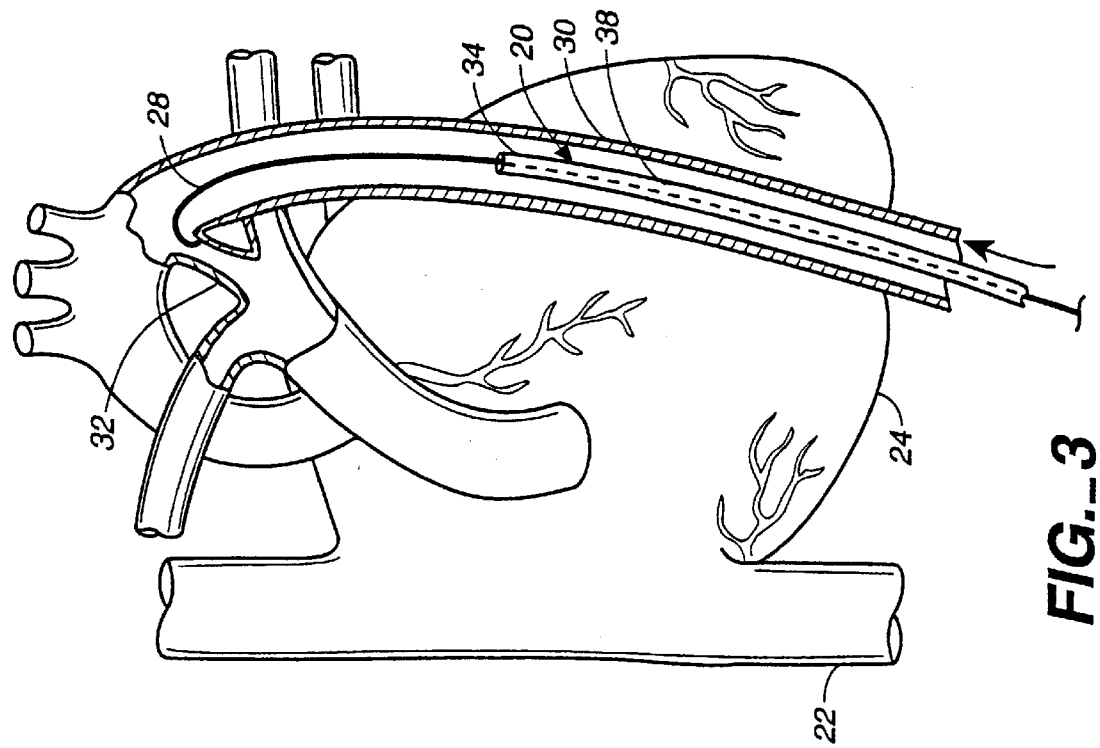
FIG._3
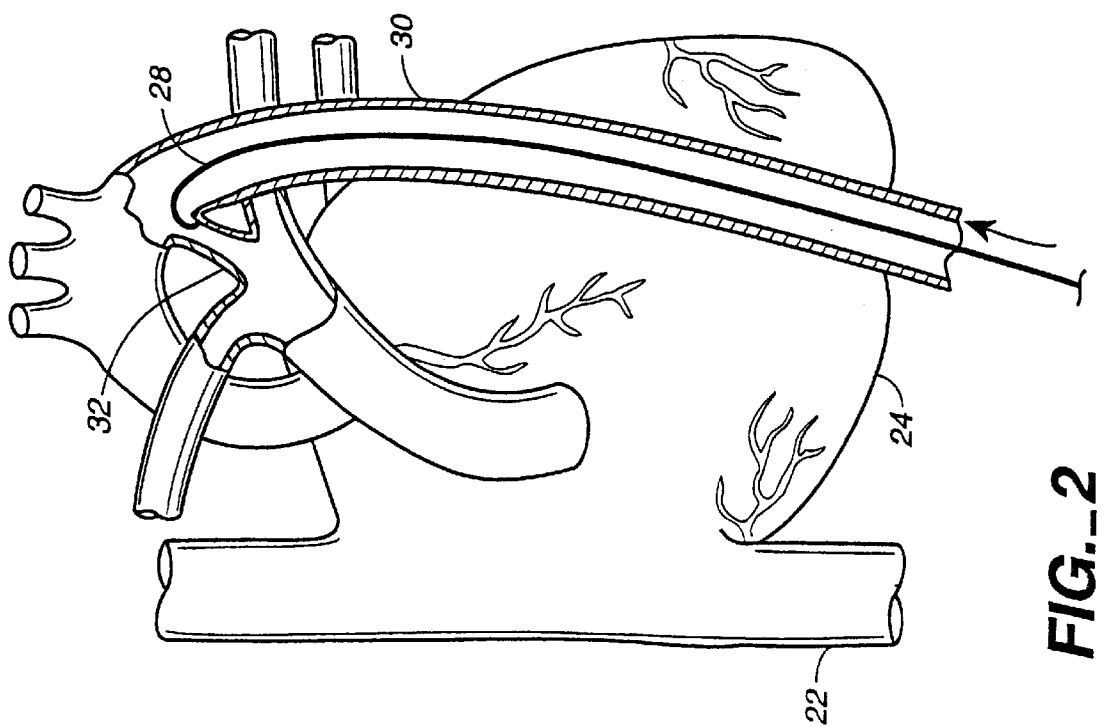
FIG._2

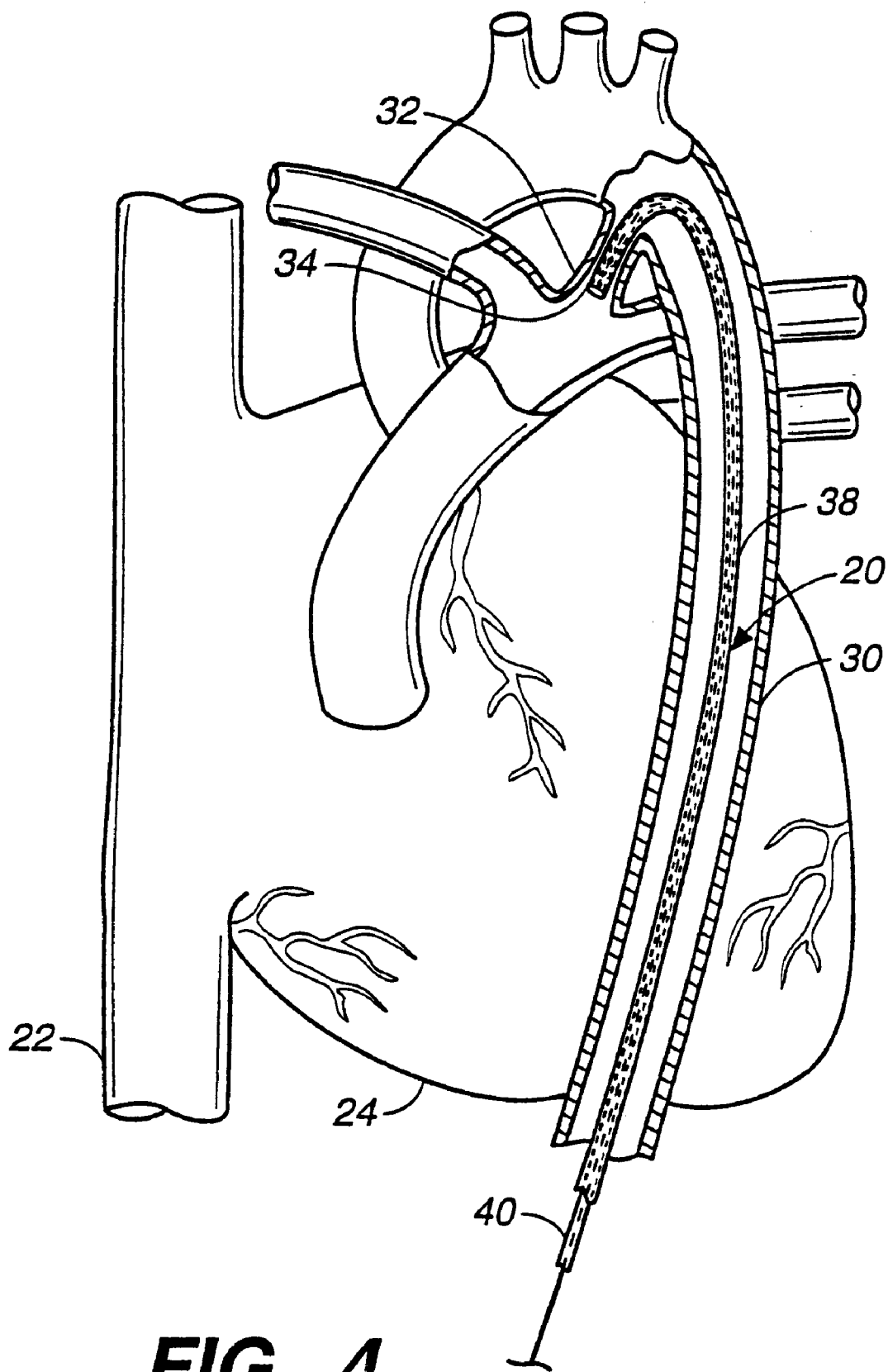
FIG._4

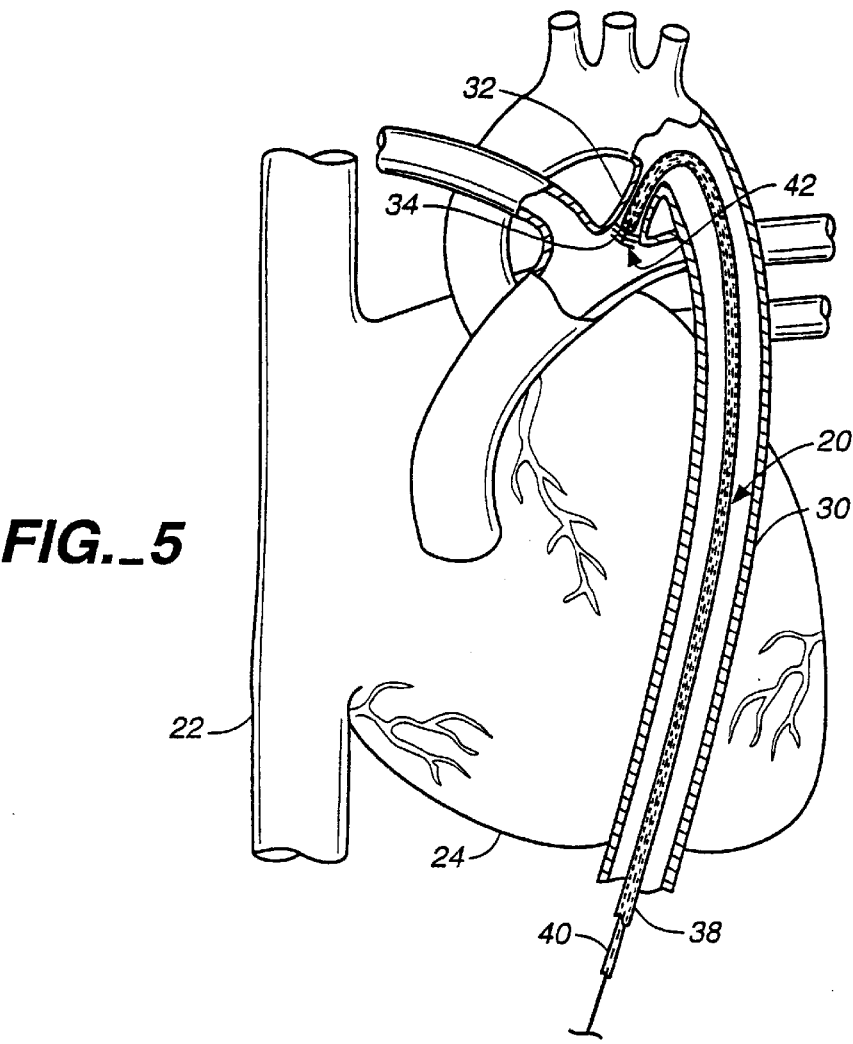
FIG._5
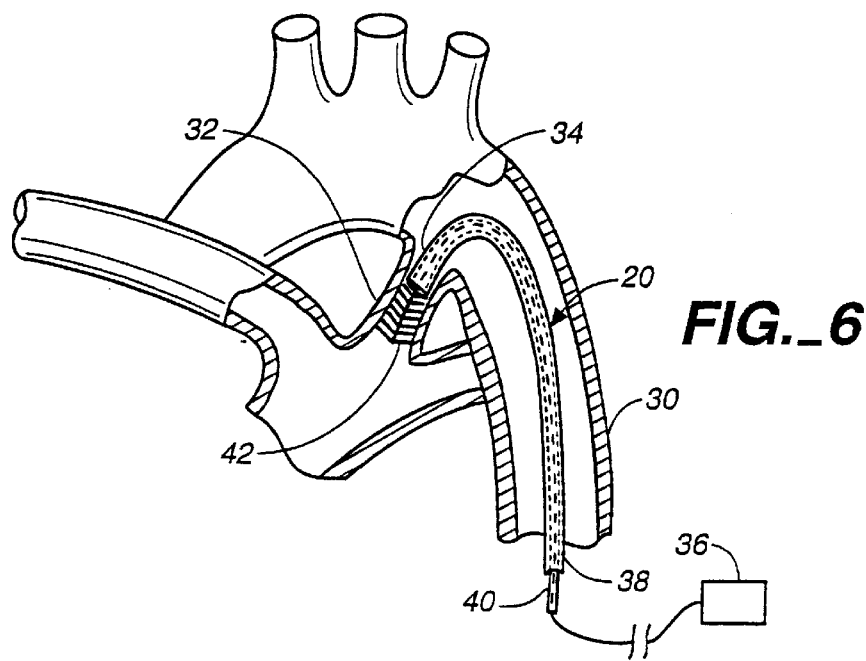
FIG._6

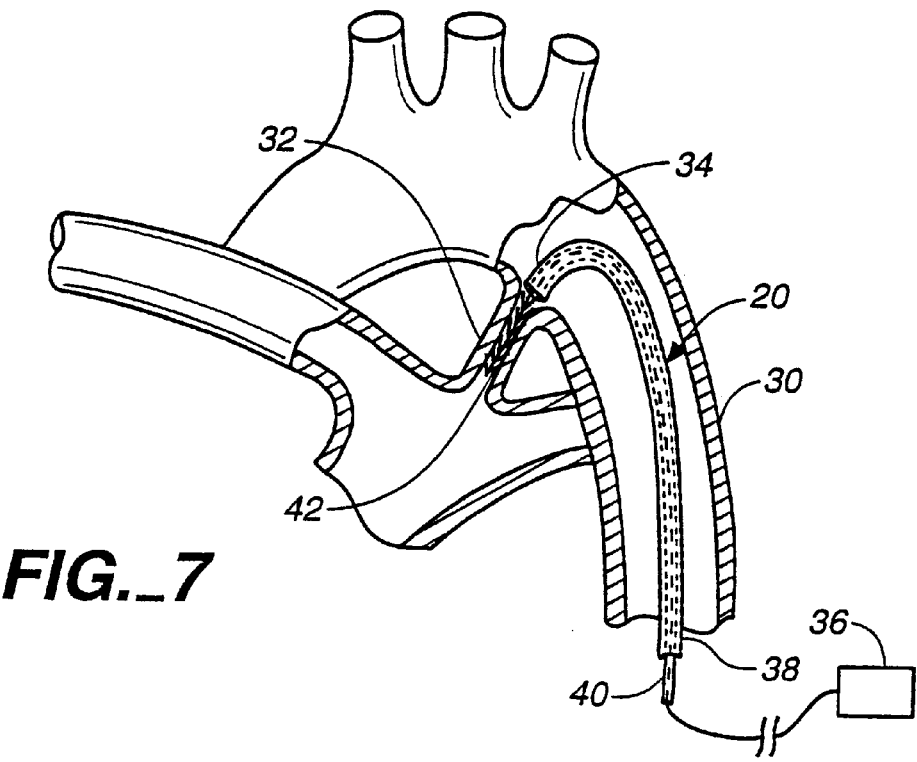
FIG._7
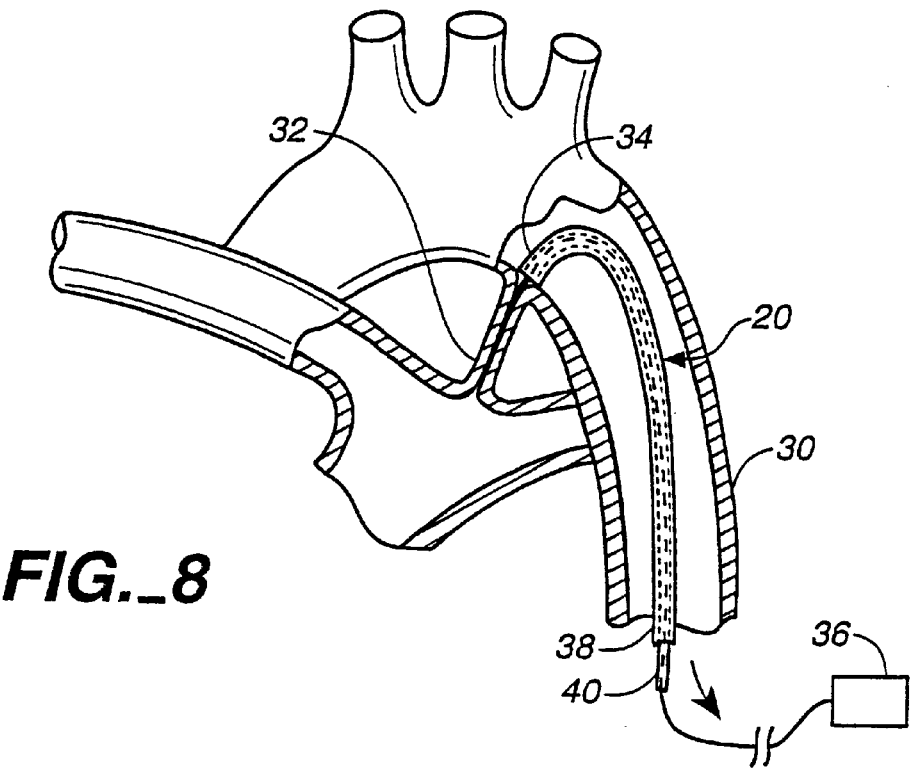
FIG._8

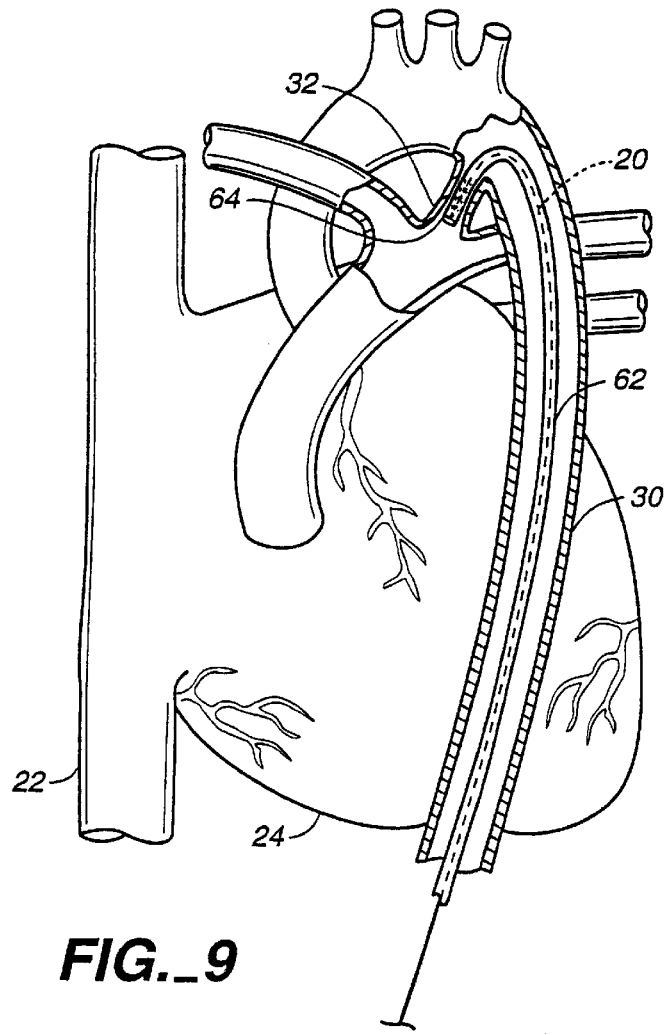
FIG._9
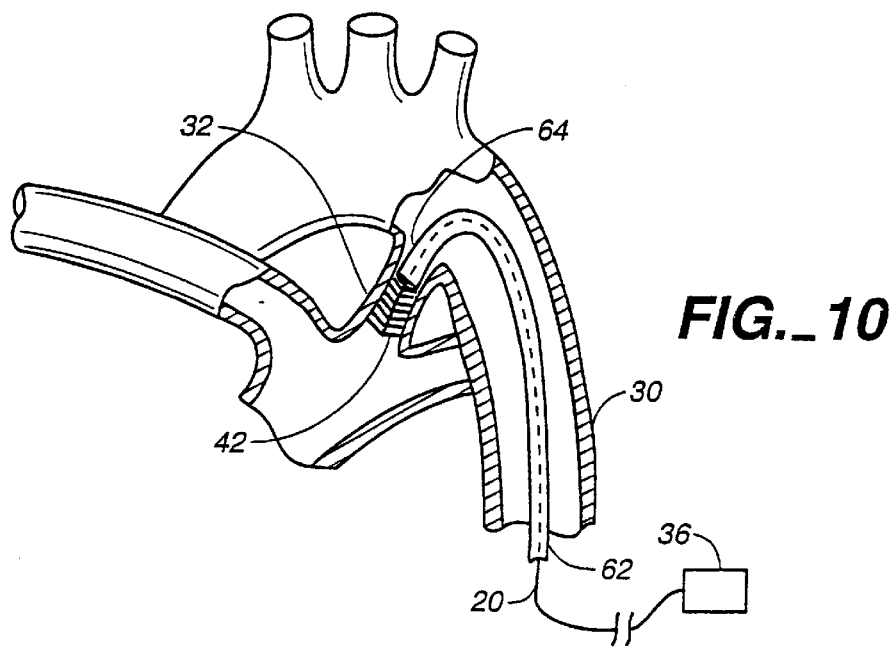
FIG._10

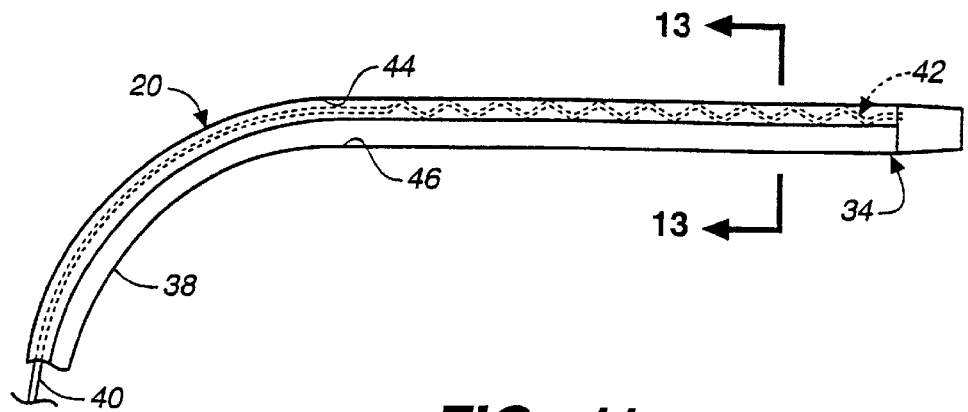
FIG._11
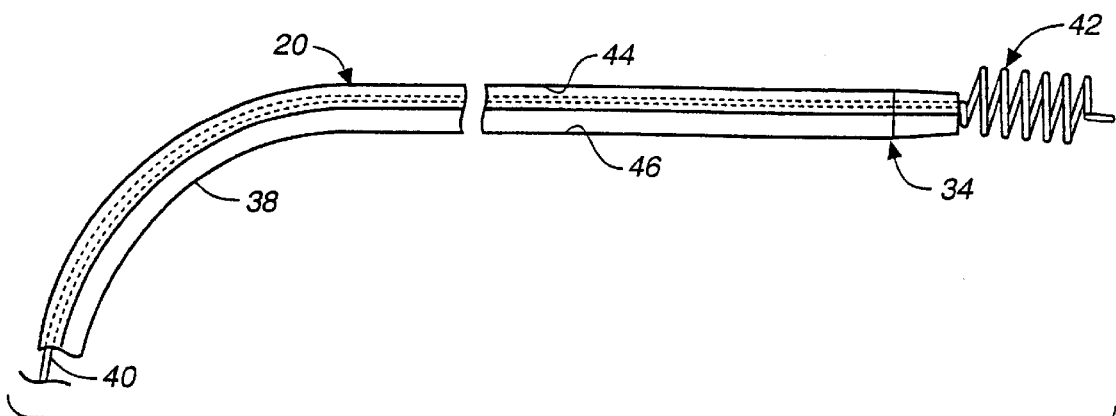
FIG._12
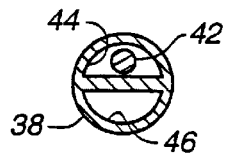
FIG._13
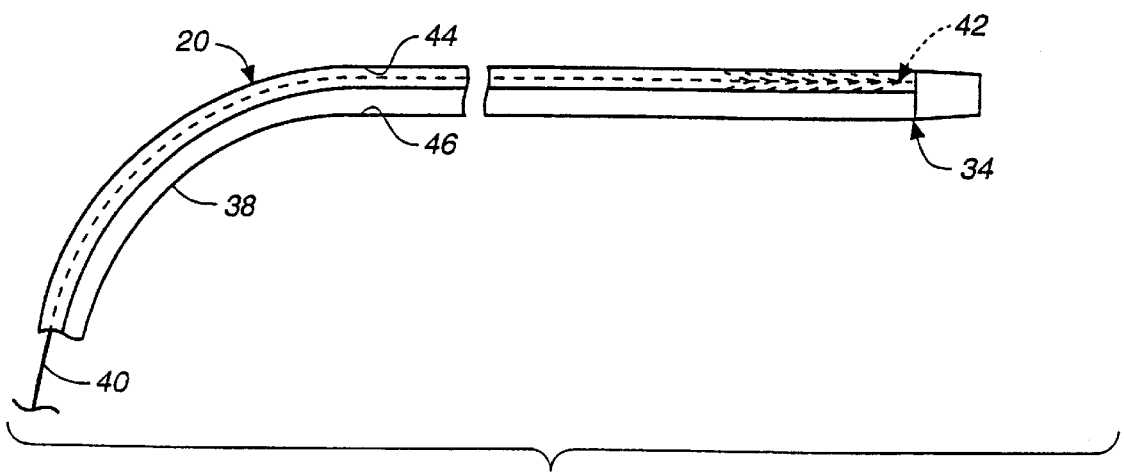
FIG._14

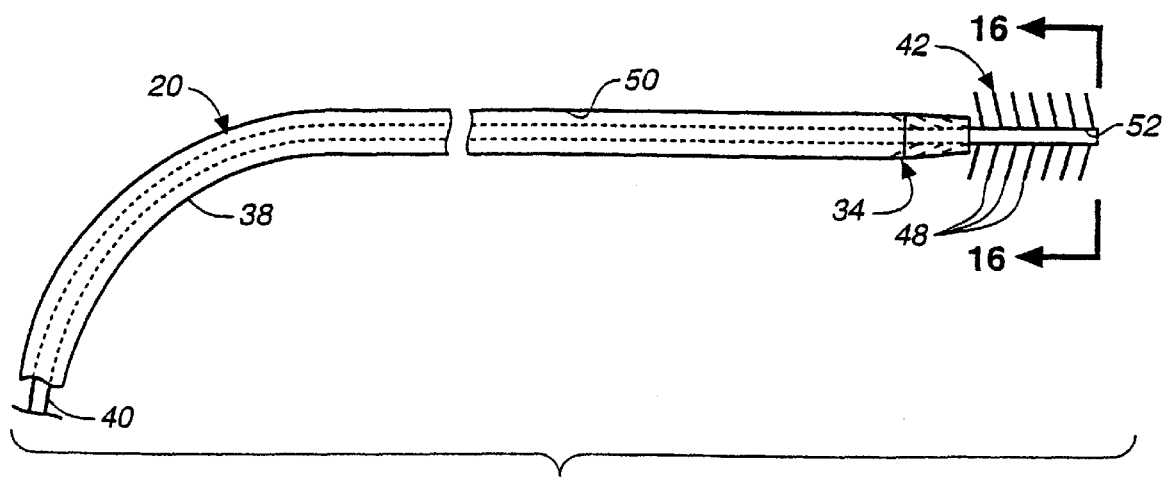
FIG._15
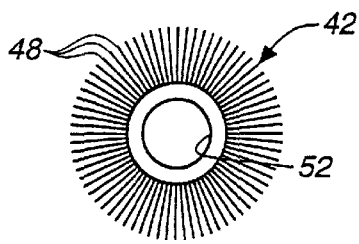
FIG._16
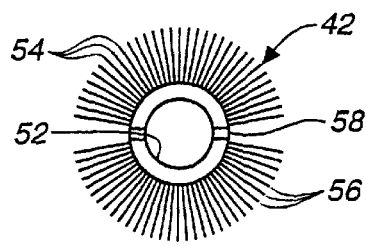
FIG._17
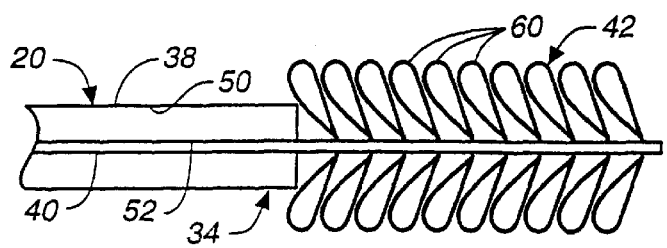
FIG._18

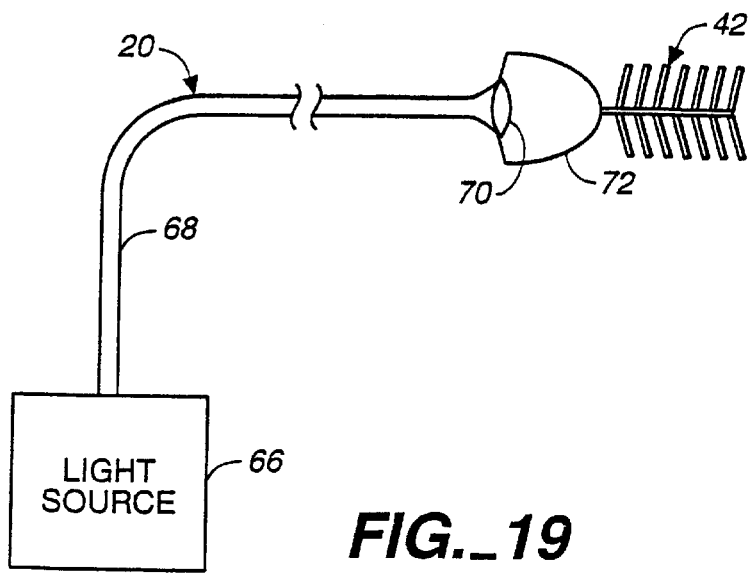
FIG._19
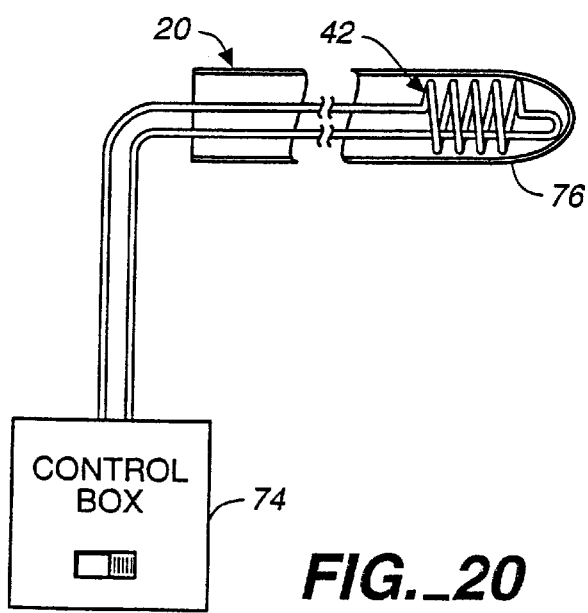
FIG._20
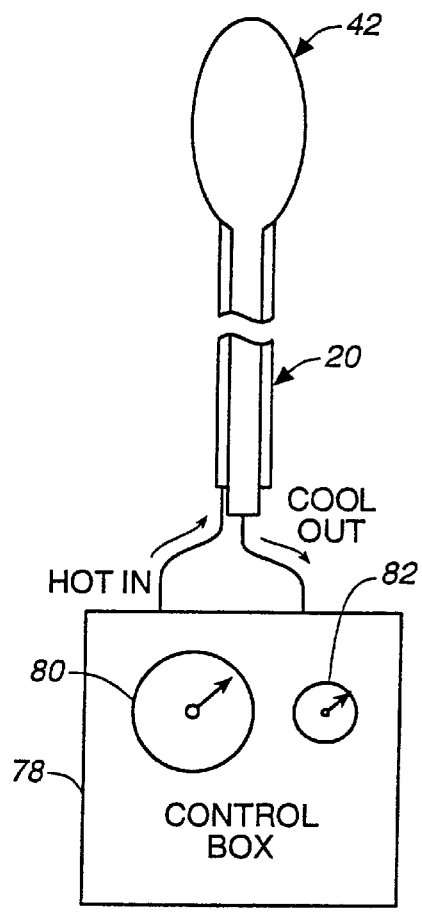
FIG._21

METHOD FOR THE TREATMENT OF PATENT DUCTUS ARTERIOSUS

This application is a continuation of application Ser. No. 08/739,820, filed Oct. 30, 1996, now U.S. Pat. No. 5,827,268.

FIELD OF THE INVENTION

The present invention is related generally to the modification of heart tissue for the ligation or interruption of congenital heart defects.

BACKGROUND OF THE INVENTION

Patent ductus arteriosus is a condition resulting from the partial continuation of fetal circulation. A fetus does not use its own lungs to oxygenate its blood, rather the fetus' blood bypasses the lungs and is oxygenated by the placenta. The ductus arteriosus allows blood to flow between the pulmonary artery and aorta in utero bypassing the non-functioning lungs during fetal development. Normally, the ductus arteriosus conduit closes naturally. This is prostaglandin dependent. If the ductus remains open, the infant has pathological shunting of blood from the systemic to the pulmonary system. This results in pulmonary hypertension which if uncorrected can result in the infant's disability and death.

Surgical procedures have been developed for closing the ductus which involve open heart surgery. The chest of the infant is opened to expose the ductus. A suture is tied around the ductus to seal it closed. For obvious reasons, open heart surgery is not desirable if alternatives exist.

Although other methods of occluding defects, most notably the use of a plastic plug to occlude the defect, were suggested as early as the 1950's, such methods similarly require the use of open heart surgery to access the defect and place the prosthetic implant.

Beginning in the early 1970's, a number of devices and methods were proposed for the percutaneous transluminal catheterization procedure for the repair of intracardiac defects. For example, U.S. Pat. No. 3,874,388 to King, et al., describes a device in which a pair of umbrella-like occluders are positioned on opposite sides of a defect and drawn and locked together at a central hub which crosses the defect. Although the King device and method proposed to eliminate the need to perform open heart surgery, use of the device was complicated in that generally the device required the umbrella-like occluders to be opened manually once positioned at the defect.

Collagen-containing connective tissue is ubiquitous in the human body and demonstrates several unique characteristics not found in other tissues. It provides the cohesiveness of the musculoskeletal system, the structural integrity of the viscera as well as the elasticity of integument. Intermolecular cross links provide collagen connective tissue with unique physical properties of high tensile strength and substantial elasticity. A previously recognized property of collagen is shrinkage of collagen fibers when elevated in temperature. This unique molecular response to temperature elevation is the result of rupture of the collagen stabilizing cross links and immediate contraction of the collagen fibers to about one-third of their original linear dimension. Additionally, the caliber of the individual fibers increases greatly, over four fold, without changing the structural integrity of the connective tissue.

There has been discussion in the existing literature regarding alteration of collagen connective tissue in different parts of the body. One known technique for effective use of this knowledge of the properties of collagen is through the use of infrared laser energy to effect tissue heating. The use of infrared laser energy as a corneal collagen shrinking tool of the eye has been described and relates to laser keratoplasty, as set forth in U.S. Pat. No. 4,976,709. The importance of controlling the localization, timing and intensity of laser energy delivery is recognized as paramount in providing the desired soft tissue shrinkage effects without creating excessive damage to the surrounding non-target tissues.

Another known technique of altering collagen is described in U.S. Pat. No. 5,458,596 to treat joints. U.S. Pat. No. 5,437,664 describes using a catheter for venous occlusion and coagulation of blood, but does not contemplate treating patent ductus arteriosus by shrinking the vessel to closure.

SUMMARY OF THE INVENTION

The present invention provides a safe, cost-effective method for treating patent ductus arteriosus in a human using selectively applied heat. Generally speaking, the present invention provides a device and method for treating patent ductus arteriosus in a human. The catheter has a heating element at a distal end for entering a human transcutaneously which is advanced to the ductus arteriosus. The method involves heating the inner surface of the ductus arteriosus with the heating element to a temperature sufficient to produce a material change in the collagen of the ductus arteriosus such that the ductus arteriosus conduit shrinks to closure. The treatment is accomplished by applying heat to the inner surface of the ductus arteriosus to collapse the ductus arteriosus passage.

In one aspect of the invention, there is provided a method for closing a patent ductus arteriosus of a patient by entering the vascular system of the patient, advancing a catheter having a heating element associated with a distal end portion through the vascular system of the patient into the ductus arteriosus, positioning the heating element within the ductus arteriosus at a first position, and energizing the heating element to effect a temperature in the ductus arteriosus sufficient to reduce at least a first portion of the ductus arteriosus passage.

In another aspect of the invention, there is provided a method for closing a patent ductus arteriosus of a patient by entering the vascular system of the patient, advancing a catheter comprising a heating element and moveable sleeve through the vascular system of the patient into the ductus arteriosus, positioning a distal end of the catheter within the ductus arteriosus at a first position, retracting the sleeve to expose the heating element to a first portion of an inside surface of the ductus arteriosus, energizing the heating element to effect a temperature in the ductus arteriosus sufficient to alter the size of the ductus arteriosus passage such that at least the first portion of a passage through the ductus arteriosus is reduced, withdrawing the heating element to further reduce the ductus arteriosus passage with a tip of the heating element, retracting the heating element into the sleeve, and withdrawing the catheter from the patient.

In still another aspect of the invention, there is provided an apparatus for closing a patent ductus arteriosus of a patient having a heating element which has a collapsible distal end portion, the distal end portion being collapsible as the ductus arteriosus passage is reduced.

BRIEF DESCRIPTION OF THE DRAWINGS

As used herein, like reference numerals will designate similar elements in the various embodiments of the present invention wherein:

FIG. 1 is a diagrammatic partial cross-sectional view of a heart with a J-tipped guidewire inserted through the femoral artery;

FIG. 2 is a diagrammatic partial cross-sectional view of the heart with the distal end of the J-tipped guidewire advanced to the opening to the ductus arteriosus;

FIG. 3 is a diagrammatic partial cross-sectional view of the heart with the distal end of the J-tipped guidewire located in the ductus arteriosus and a catheter in accordance with one embodiment of the present invention being advanced over the J-tipped guidewire;

FIG. 4 is a diagrammatic partial cross-sectional view of the heart with the distal end of the catheter of FIG. 3 located in the ductus arteriosus;

FIG. 5 is a diagrammatic partial cross-sectional view of the heart with a sleeve of the catheter of FIG. 3 being retracted to expose a portion of a heating element in accordance with one embodiment of the present invention;

FIG. 6 is a diagrammatic partial cross-sectional view of a portion of the heart with the outer sleeve of FIG. 3 retracted to expose the heating element;

FIG. 7 is a diagrammatic partial cross-sectional view of a portion of the heart showing the ductus arteriosus passage collapsing on the heating element;

FIG. 8 is a diagrammatic partial cross-sectional view of the portion of the heart showing the ductus arteriosus passage collapsed and the heating element being retracted into the sleeve;

FIG. 9 is a diagrammatic partial cross-sectional view of the heart with the distal end of a guide catheter of an alternate embodiment located in the ductus arteriosus;

FIG. 10 is a diagrammatic partial cross-sectional view of a portion of the heart with the guide catheter sleeve of FIG. 9 retracted to expose the expandable heating element;

FIG. 11 is a diagrammatic representation of one embodiment of the catheter of the present invention with a heating element located in a sleeve;

FIG. 12 is a diagrammatic representation of the catheter of FIG. 11 with the sleeve retracted to expose the heating element;

FIG. 13 is a cross-sectional view taken along line 13—13 of FIG. 11;

FIG. 14 is a diagrammatic representation of another embodiment of the catheter of the present invention with the heating element located in the sleeve;

FIG. 15 is a diagrammatic representation of yet another embodiment of the catheter of the present invention with the sleeve partially retracted to expose a portion of the heating element;

FIG. 16 is a end view taken along line 16—16 of the heating element of FIG. 15;

FIG. 17 is an end view of an alternate embodiment of the heating element of FIG. 16;

FIG. 18 is a diagrammatic representation of still another embodiment of the catheter of the present invention with the sleeve retracted to expose the heating element;

FIG. 19 is a diagrammatic representation of yet another embodiment of the catheter of the present invention;

FIG. 20 is a diagrammatic representation of still another embodiment of the catheter of the present invention; and FIG. 21 is a diagrammatic representation of another embodiment of the catheter of the present invention.

DETAILED DESCRIPTION OF THE PREFERRED EMBODIMENTS

The present invention provides a device and method for effecting change in collagen-containing soft tissue in a patent ductus arteriosus of a human. The ductus arteriosus is a vessel having arterial characteristics in that the ductus arteriosus has two layers of muscular and collagen connective tissue. The invention accurately controls the application of heat within a specific thermal range, and delivers thermal energy to the collagen-containing soft tissue of the ductus arteriosus to close off the ductus arteriosus to blood flow without ablating the tissue.

Referring initially to FIGS. 1–8 which illustrate the placement of catheter 20 within the patent ductus arteriosus 32 of a heart 24. Guidewire 28 (and subsequently catheter 20) is inserted in the illustrated embodiment through a femoral artery 26 or vein using the Seldinger technique or a cut-down technique. Alternatively, the guidewire 28 and subsequently catheter 20 can be inserted through a brachial artery or vein (not shown) in the arm to gain access to the ductus arteriosus. The guidewire 30 is advanced through the aorta 30 using conventional fluoroscopic guidance. Preferably, the guidewire 28 is a J-tipped guidewire to facilitate advancing the guidewire into the opening of the ductus arteriosus 32 (FIG. 2). However, other configurations of guidewires or other techniques can be used to gain entry into the ductus arteriosus 32 by the catheter 20, for example through the vena cava 22. The guidewire 28 is advanced into the ductus arteriosus 32 (FIG. 3). The catheter 20 of the present invention is inserted through the femoral artery 26 and advanced over the guidewire 28 using conventional techniques into the ductus arteriosus 32 (FIG. 4). After the distal end 34 of catheter 20 is inserted into the desired location in the ductus arteriosus 32, guidewire 28 is retracted through the catheter. The desired location may be a fully inserted position in the ductus arteriosus 32 as shown in FIG. 4, an intermediate position (not shown) in the ductus arteriosus, or in the opening of the ductus arteriosus (not shown).

Catheter 20 is sufficiently long to extend from a fully inserted position in the ductus arteriosus 32 to an RF generator 36 located remotely from the patient. Catheter 20 has a sleeve 38 that extends along a part of that length from a fully inserted position in the ductus arteriosus 32 to a convenient point outside of the insertion point in the patient such that the surgeon performing the procedure can grasp and manipulate the sleeve 38. The surgeon retracts the sleeve 38 over a conductor 40 that is connected to RF generator 36 to expose a heating element 42 associated with the distal end of the catheter 20. Alternatively, the catheter 20 can be inserted intermediately in the ductus arteriosus 32 or at the opening of the ductus arteriosus and the conductor 40 can be pushed out of the distal end of the sleeve 38. The ductus arteriosus generally has a length in the range of 2 millimeters to 3 centimeters, accordingly the length of the collapsible portion of the heating element 42 in accordance with any of the embodiments described below is in the range of about 2 millimeters to about 3 centimeters.

Preferably, the outer diameter of the catheter 20 is smaller than the inside diameter of the ductus arteriosus 32 so that the catheter 20 passes atraumatically into the ductus arteriosus 32. The heating element 42 is expandable (preferably self-expanding) and has an outer diameter larger than the outer diameter of the catheter 20 and the inner diameter of the ductus arteriosus 32 such that when the surgeon retracts the sleeve 38 (or advances the conductor 40), the heating element 42 expands to contact the inside surface of the ductus arteriosus 32 (FIG. 6). The heating element 42 can extend the entire length of the ductus arteriosus 32 as shown in FIGS. 6–8, or can extend only along a portion of the ductus arteriosus. In the second situation, the steps described below could be repeated as many times as desired by the surgeon to accomplish closure along the length of the ductus arteriosus. The heating element 42 is energized to bring about shrinkage of the ductus arteriosus passage such that the ductus arteriosus closes around the heating element which in turn also collapses.

Referring to FIGS. 9 and 10, an alternate embodiment for the catheter 20 and method of placement of the catheter 20 within the patent ductus arteriosus 32 of a heart 24 is shown. A guidewire (not shown) is inserted and advanced to the ductus arteriosus using conventional fluoroscopic guidance as described above through a femoral artery 26 or vein using the Seldinger technique or a cut-down technique. Alternatively, the guidewire and subsequently catheter 20 can be inserted through a brachial artery or vein (not shown) in the arm to gain access to the ductus arteriosus. A guide sleeve 62 is inserted through the femoral artery 26 and advanced over the guidewire (not shown) using conventional techniques into the ductus arteriosus. After the distal end 64 of guide sleeve 62 is inserted into the desired location in the ductus arteriosus 32, the guidewire is retracted through the guide sleeve. The desired location may be a fully inserted position in the ductus arteriosus 32 as shown in FIG. 9, an intermediate position (not shown) in the ductus arteriosus, or in the opening of the ductus arteriosus (not shown). Catheter 20 is then inserted into and advanced through the guide sleeve 62 to the desired location using conventional fluoroscopic techniques.

Catheter 20 is sufficiently long to extend from a fully inserted position in the ductus arteriosus 32 to an RF generator 36 located remotely from the patient (FIG. 10). Guide sleeve 62 has a length that extends along a part of the catheter length from a fully inserted position in the ductus arteriosus 32 to a convenient point outside of the insertion point in the patient such that the surgeon performing the procedure can grasp and manipulate the guide sleeve 62. The surgeon retracts the guide sleeve 62 over the catheter 20 that is connected to RF generator 36 to expose the heating element 42 associated with the distal end of the catheter 20. Alternatively, the guide sleeve 62 can be inserted intermediately in the ductus arteriosus 32 or at the opening of the ductus arteriosus and the catheter 20 can be pushed out of the distal end of the guide sleeve 62.

Preferably, the outer diameter of the guide sleeve 62 is smaller than the inside diameter of the ductus arteriosus 32 so that the guide sleeve 62 passes atraumatically into the ductus arteriosus 32 over the guidewire (not shown). Preferably, the heating element 42 is expandable (preferably self-expanding) and has an outer diameter larger than the outer diameter (accordingly, the inner diameter) of the guide sleeve 62 such that the heating element is compressed as it is inserted through the guide sleeve. Likewise, the heating element 42 has an outer diameter larger than the inner diameter of the ductus arteriosus 32 such that when the surgeon retracts the guide sleeve 62 (or advances the catheter 20), the heating element 42 expands to contact the inside surface of the ductus arteriosus 32 (FIG. 10). The heating element 42 can extend the entire length of the ductus arteriosus 32 as shown in FIGS. 6–8, or can extend only along a portion of the ductus arteriosus as shown in FIGS. 9–10.

After completing the procedure for closing off the ductus arteriosus, the heating element 42 is withdrawn into the sleeve 38 and the catheter 20 is then removed from the patient. The access point for the guidewire and catheter is sutured closed if a cutdown had been performed, or local pressure is applied until bleeding is controlled if the Seldinger technique was used. A bandage is then applied. A pressure dressing may be applied if necessary.

Preferably, heating element 42 is an RF electrode located at the distal end of the catheter 20. Alternatively, the method is contemplated to be used with any suitable appliance for applying radiant energy, thermal energy, or to otherwise heat the tissue in a patent ductus arteriosus and shrink the ductus arteriosus conduit to closure. When the heating element 42 of the catheter 20 is positioned at the treatment site of the patent ductus arteriosus 32, the RF generator 36 is activated to provide suitable RF energy, preferably at a selected frequency in the range of 10 megahertz to 1000 megahertz. One criteria for the selection of the applied frequency is the absence or minimization of coagulation in the ductus arteriosus. The emitted energy is converted within the tissue of the ductus arteriosus into heat in the range of about 50 degrees Celsius to about 98 degrees Celsius. As the temperature of the ductus arteriosus tissue increases, the ductus arteriosus passage begins to shrink without rupture or perforation of the ductus arteriosus. The shrinkage is apparently due, without being limited to a theory, in part to dehydration and in part to the structural transfiguration of the collagen fibers in the vessel. Although the collagen becomes compacted during this process, the collagen still retains some elasticity. When RF energy is applied, shrinkage of the ductus arteriosus reduces the patency. As the ductus arteriosus 32 shrinks inward on the heating element 32, the heating element collapses to a diameter just greater than the diameter of the conductor 40. As the heating element 32 collapses to a diameter just greater than the diameter of the conductor 40, the conductor 40 is withdrawn. As the conductor 40 is withdrawn, the remainder of the ductus arteriosus will close at the distal tip of the heating element 32 as the tip becomes the focal point of the current. In this way, the focusing of the heat at the tip of the heating element closes off the ductus arteriosus.

RF energy is no longer applied after there has been sufficient shrinkage of the ductus arteriosus passage to close off the ductus arteriosus to the flow of blood. Sufficient shrinkage may be detected by fluoroscopy, external ultrasound scanning, pulse-echo ultrasound scanning, sensing the collapsing or straightening of the heating element with appropriate feed back variables, impedance monitoring, temperature monitoring, direct visualization using an angioscope, or any other suitable method.

Substantial shrinkage may be achieved very rapidly, depending upon the specific treatment conditions. Because the shrinkage can proceed at a rather rapid rate, the RF energy is preferably applied at low power levels. The RF power is preferably applied in the range of about 1 watt to about 10 watts. Preferably, the RF energy is applied for a length of time in the range of about 10 seconds to about 120 seconds. The frequency of the RF energy is selected to minimize coagulation at the treatment site. Suitable RF power sources are commercially available and well known to those skilled in the art. In one embodiment of the invention RF generator 36 has a single channel, delivering approximately 1 to 10 watts of RF energy and possessing continued flow capability. The rate of shrinkage of the ductus arteriosus can be controlled by increasing or decreasing blood flow/infusion around the catheter, varying the energy delivered to the heating element, and/or selecting stiffer or more flexible collapsible elements for the heating element to stent the ductus arteriosus while the ductus arteriosus shrinks closed.

The heating element 42 can be made to provide protection against overheating of the ductus arteriosus. In one embodiment, the heating element has a shape memory capability such that the heating element self-straightens or collapses if the heating element or the blood reaches a temperature above 98 degrees Celsius such that contact with the inner surface of the ductus arteriosus would be lost, the heating element would cover with coagulum and the current flow through the heating element would become nearly zero.

The catheter 20 and heating element 42 preferably are constructed from materials which would allow visualization under fluoroscopy, x-ray, ultrasound, or other imaging techniques. Preferably, closure of the ductus arteriosus is detected by fluoroscopy or external ultrasound techniques. For example, a contrast medium may be injected into the ductus arteriosus to assess the condition of the ductus arteriosus and the relationship of the catheter to the treatment area of the ductus arteriosus by contrast radiography during the closure process. The catheter 20 can be configured to deliver x-ray contrast medium to allow visualization by fluoroscopy. As an alternative to fluoroscopy, external ultrasounding techniques such as B-mode scanning using distinct ultrasound signals from different angles, can be used to acquire a more multi-dimensional view of the ductus arteriosus shrinkage at the treatment site, which improves the detection of uneven shrinkage in the ductus arteriosus. An angioscope may also be used to directly visualize and determine the extent and degree of ductus arteriosus closure. The shrinkage can be monitored and the collapsing of the heating element controlled to ensure the heating element remains in contact with the ductus arteriosus during the process.

Other techniques, for example, temperature monitoring, impedance monitoring, and ultrasonic pulse echoing, can be utilized in a system which shuts down the application of energy from the heating element to the ductus arteriosus section when sufficient closure of the ductus arteriosus is detected and to avoid burning of the ductus arteriosus. Monitoring these values for feedback control of the energy applied also minimizes coagulation. The amount of energy applied can be decreased or eliminated (manually or automatically) if coagulation begins to occur. For example, the temperature of the blood, ductus arteriosus tissue, or of heating element 42 is monitored and the energy being applied adjusted accordingly. The surgeon can, if desired, override the feedback control system. A microprocessor can be included and incorporated into the feedback control system to switch the power on and off, as well as modulate the power. The microprocessor can serve as a controller to watch the temperature and modulate the power in order to minimize coagulation.

Although the invention has been described as using RF energy for energizing the heating element, it is to be understood that other forms of energy such as alternating current, microwaves, ultrasound, and light (either coherent or incoherent sources) can be used, and that the thermal energy generated from a resistive coil, a hot fluid element (e.g., liquids, gases, combinations of liquids and gases, etc.), a curie point element, or similar elements can be used as well. The delivery of the thermal energy to the ductus arteriosus should be delivered in such a way that none of the tissue is ablated and/or the collapsing of the ductus arteriosus passage occurs without rupture or perforation of the ductus arteriosus.

Referring now to FIGS. 11–13, an embodiment of the catheter 20 is shown having a heating element 42 disposed within a dual lumen sleeve 38 at the tapered distal end 34 of the catheter. The sleeve 38 is soft and flexible so as to be passed atraumatically through the vascular system to the ductus arteriosus and so as to be able to traverse the tortuous path of the vascular system to the ductus arteriosus. Catheter 20 has an outside diameter in the range of about 1.5 millimeters to 7 millimeters.

Heating element 42 as illustrated in FIGS. 11 and 12 is an expandable and collapsible heating element of a curled configuration (e.g., a helix, coil, corkscrew, spiral, twist, etc.). Preferably, the heating element is a biocompatible material with at least partial shape memory capability, such as a nickel-titanium-based alloy. Heating element 42 in accordance with any of the embodiments can be a number of different materials including but not limited to conductive polymer, stainless steel, platinum, other noble metals, or shape memory alloy, such as nickel-titanium-alloy (Nitinol™ commercially available from Raychem Corporation, Menlo Park, Calif.).

The heating element 42 and its corresponding conductor 40 are slidable within first lumen 44 of sleeve 38. Second lumen 46 slidably receives a guidewire so that catheter 20 can be advanced to the ductus arteriosus over the guidewire as described previously. The inside diameter of first lumen 44 is smaller than the outside diameter of the expanded, curled heating element 42 as shown in FIG. 12. As a result, when the curled heating element 42 is retracted into the first lumen 44 of sleeve 38, the curl becomes compressed and elongated as shown in FIG. 11. Correspondingly, as the sleeve 38 is retracted to expose the curled heating element 42 as shown in FIG. 12 the heating element 42 expands to contact the inside surface of the ductus arteriosus as described previously. The diameter of the first lumen is preferably in the range of about 2 French to 7 French. The diameter of the second lumen is preferably in the range of about 0.015 inches to 0.030 inches. The diameter of the expanded heating element is preferably in the range of about 1.5 millimeters to 7 millimeters.

Referring now to FIGS. 15 and 16, there is another embodiment of the catheter 20 (as shown in FIGS. 1–8) having a heating element 42 disposed within a sleeve 38 at the tapered distal end 34 of the catheter. As described above, the sleeve 38 is soft and flexible. Catheter 20 of this embodiment has an outside diameter in the range of about 1.5 millimeters to 7 millimeters.

Heating element 42 as illustrated in FIGS. 15 and 16 is an expandable and collapsible heating element comprised of a plurality of conductive elements 48 (e.g., soft bristles, fibers, "hairs", etc.). The conductive elements 48 are soft and pliable so as to not perforate or otherwise damage the ductus arteriosus and so as to be collapsible. The heating element 42 and its corresponding conductor 40 are slidable within lumen 50 of sleeve 38. Inside of heating element 42 and its corresponding conductor 40 is lumen 52 which slidably receives a guidewire. The inside diameter of lumen 50 is smaller than the outside diameter of the expandable heating element 42 as shown in FIG. 15. As a result, when the expandable heating element 42 is retracted into the lumen 50 of sleeve 38, the conductive elements 48 are forced to fold down. Correspondingly, as the sleeve 38 is retracted to expose the expandable heating element 42 the conductive elements 48 expand to contact the inside surface of the ductus arteriosus. The diameter of the lumen 50 is preferably in the range of about 2 French to 7 French. The diameter of the lumen 52 is preferably in the range of about 0.015 inches to 0.030 inches. The diameter of the expanded heating element is preferably in the range of about 1.5 millimeters to 7 millimeters.

In FIG. 14, there is illustrated an embodiment similar to FIGS. 15 and 16, except that the expandable and collapsible heating element 42 and conductor 40 are smaller in diameter and thus do not have a lumen through their length thereof. For this embodiment, a dual lumen sleeve 38 as described with respect to FIGS. 11–13 is used so that expandable heating element 42 and conductor 40 slide in first lumen 44 and a guidewire (not shown) can be used in the second lumen 46.

The heating element 42, as shown in FIGS. 1–16, operates as a unipolar, internal electrode in the patient's body. An outer electrode (not shown) having a much larger surface area than the heating element 42 is placed on the outer surface of the patient's body. For example, an external metal mesh or solid plate is placed on the skin. Both electrodes are connected to RF generator 36 which produces an electric field at a high frequency within the patient's body. Because the surface area of the heating element 42 is much smaller than that of the outer electrode, the density of the high frequency electric field is much higher around the heating element. The electric field reaches its highest density between the two electrodes in the region near the heating element 42. The increased density of the field around the heating element 42 produces localized heating of the tissue of the ductus arteriosus.

A bipolar electrode as shown in FIG. 17 can also be used. The heating element 42 and conductor 40 are similar to that described with respect to FIGS. 15 and 16 with a plurality of conductive elements and lumen 52, except that in the embodiment of FIG. 17 the conductive elements are divided into a first set of conductive elements 54 and a second set of conductive elements 56. In the bipolar arrangement, the heating element 42 emits RF energy with the first set of conductive elements 54 and the second set of conductive elements 56. The first set of conductive elements 54 can act as the active electrode, and the second set of conductive elements 56 can act as the return electrode, or vice versa. An insulator 58 is located between the first set of conductive elements 54 and the second set of conductive elements 56. While the conductive elements 54 and 56 have been shown as soft bristles, fibers, or "hairs", other configurations and arrangements can be used. For example, as shown in FIG. 18, a plurality of loops 60 can be used as the conductive elements in either a unipolar or bipolar configuration. Similarly, any of the conductive elements 48, 54, 56 and/or 60 can be angled rearward (as shown), forward, both, or not angled. The bipolar arrangement of active and return elements can be twisted around the conductive element 40 to distribute the positively and negatively charged elements around the catheter. Any of the conductive elements 48, 54, 56 and/or 60 can be electrically conductive materials or can be non-conductive materials (such as mylar, PTFE, etc.) coated with graphite or other electrically conductive coating.

FIG. 19 is a diagrammatic representation of another embodiment of the present invention wherein the expandable and collapsible heating element 42 like that described with respect to FIG. 14 is heated with a light source 66, for example, a laser or halogen source. The light source 66 transmits light via fiber optic light pipe 68 to lens 70 which diffuses the light onto parabolic heat sink 72 to convert the light energy to heat in the heating element 42.

FIG. 20 is a diagrammatic representation of a resistive heating element embodiment of the present invention. Heating element 42 is a expandable and collapsible coil which is connected to an energy control box 74 which provides resistive heating to the coil. An optional protective sheath 76 (such as Teflon®) can be provided over the heating element.

FIG. 21 is a diagrammatic representation of a hot fluid heating element 42 and control box 78 for controlling and regulating the heat applied. Hot fluid is injected into the balloon heating element 42 and circulated out through the cooler side of the catheter 20. As the ductus arteriosus passage closes, the balloon heating element 42 collapses and less fluid is circulated through the heating element 42 as the volume of the heating element 42 decreases. Control box 78 has a temperature gauge 80 and pressure gauge 82 for monitoring the temperature and pressure, respectively, of the heating element 42. The control box 78 maintains the pressure at a constant level by controlling the circulation rate of a pump (not shown). As the ductus arteriosus closes, the volume of the balloon heating element 42 decreases increasing the pressure in the balloon. The control box 78 decreases the flow of the hot fluid in response to the increase in pressure in the balloon.

While several particular embodiments of the invention have been illustrated and described, it will be apparent that various modifications can be made without departing from the spirit and scope of the invention. Accordingly, it is not intended that the invention be limited, except as by the appended claims.

What is claimed is:

1. A method for closing a patent ductus arteriosus of a patient, comprising the steps of:

entering the vascular system of the patient;

advancing a catheter having a non-laser heating element associated with a distal end portion through the vascular system of the patient into the ductus arteriosus;

positioning the heating element within the ductus arteriosus at a first position; and energizing the heating element to reduce at least the first portion of the ductus arteriosus without ablating tissue of the ductus arteriosus.

2. The method of claim 1 further comprising:

withdrawing the catheter a sufficient distance to position the heating element at a second position; and energizing the heating element to a temperature sufficient to reduce at least a second portion of the ductus arteriosus.

3. The method of claim 1 further comprising:

sensing a predetermined parameter; and automatically decreasing the magnitude of the energy being delivered by the heating element when the predetermined parameter reaches a preselected value.

4. The method of claim 1 wherein the non-laser heating element is energized by applying radio frequency electric energy.

5. The method of claim 4 wherein the power of the radio frequency electric energy applied is in the range of about 1 watt to about 10 watts.

6. The method of claim 1 wherein the radio frequency electric energy is applied for a length of time in the range of about 10 to about 120 seconds.

7. The method of claim 1 further comprising:

focusing the energy at a distal most portion of the heating element as the ductus arteriosus closes.

8. The method of claim 1 wherein the energizing step comprises controlling the amount of energy applied such that closing occurs without rupturing or perforating the ductus arteriosus.

9. The method of claim 1 wherein the heating element is energized to a temperature in the range of about 50 degrees Celsius to about 98 degrees Celsius.

10. The method of claim 1 further comprising sensing the closing of the ductus arteriosus.

11. The method of claim 1 further comprising maintaining the heating element in contact with the ductus arteriosus as the at least first portion of the ductus arteriosus closes.

* * * * *